(12) United States Patent
Danino et al.

(10) Patent No.: US 11,350,875 B2
(45) Date of Patent: Jun. 7, 2022

(54) CUMULATIVE BIOSENSOR SYSTEM TO DETECT ALCOHOL

(71) Applicant: LOGICINK CORPORATION, San Francisco, CA (US)

(72) Inventors: Tal Danino, San Francisco, CA (US); Ian Fritz, San Francisco, CA (US); Carlos Olguin, San Francisco, CA (US); Skylar Tibbits, San Francisco, CA (US); Marcelo Coelho, San Francisco, CA (US)

(73) Assignee: LOGICINK CORPORATION, San Francisco, CA (US)

( * ) Notice: Subject to any disclaimer, the term of this patent is extended or adjusted under 35 U.S.C. 154(b) by 194 days.

(21) Appl. No.: 16/528,362

(22) Filed: Jul. 31, 2019

(65) Prior Publication Data

US 2020/0022648 A1    Jan. 23, 2020

Related U.S. Application Data

(63) Continuation of application No. PCT/CN2018/016281, filed on Jan. 31, 2018.

(Continued)

(51) Int. Cl.
*A61B 5/00* (2006.01)
*A61B 5/145* (2006.01)
(Continued)

(52) U.S. Cl.
CPC .......... *A61B 5/4845* (2013.01); *A61B 5/1477* (2013.01); *A61B 5/14517* (2013.01);
(Continued)

(58) Field of Classification Search
CPC ... A61B 5/145; A61B 5/14546; A61B 5/4845; A61B 5/72; A61B 5/7264;
(Continued)

(56) References Cited

U.S. PATENT DOCUMENTS

| 4,382,063 A | 5/1983 | Romito et al. |
| 4,788,432 A | 11/1988 | Patel |

(Continued)

FOREIGN PATENT DOCUMENTS

| WO | WO-02094098 A1 * | 11/2002 | ............. A61B 5/445 |
| WO | WO-2009149308 A2 * | 12/2009 | ....... G01N 33/54386 |

(Continued)

OTHER PUBLICATIONS

Koh, Ahyeon, et al., "A soft, wearable microfluidic device for the capture, storage, and colorimetric sensing of sweat," Nov. 2016, Science Translational Medicine, 8(366), https://stm.sciencemag.org/content/8/366/366ra165.full (Year: 2016).*

(Continued)

*Primary Examiner* — Eric F Winakur
*Assistant Examiner* — Alice Ling Zou
(74) *Attorney, Agent, or Firm* — Polsinelli LLP

(57) ABSTRACT

A wearable device may be provided for detecting cumulative alcohol consumption. Such a wearable device may include an adhesive layer that adheres to skin and that allows sweat from the skin to pass through and a customizable ink layer that reacts irreversibly to change color along a gradient as ethanol is detected in the sweat. The customizable ink continues to increase color intensity along the gradient as ethanol continues to be detected in the sweat over time.

12 Claims, 4 Drawing Sheets

Related U.S. Application Data

(60) Provisional application No. 62/452,579, filed on Jan. 31, 2017.

(51) Int. Cl.
*A61B 5/1477* (2006.01)
*A61B 5/1486* (2006.01)

(52) U.S. Cl.
CPC ........ *A61B 5/14546* (2013.01); *A61B 5/6832* (2013.01); *A61B 5/7264* (2013.01)

(58) Field of Classification Search
CPC ............ A61B 5/14517; A61B 5/14532; A61B 5/1477; A61B 5/1468; A61B 5/6801; A61B 5/6832; A61B 5/14507; A61B 5/1451; A61B 5/1486; G06K 9/46; G06K 9/36; G06K 9/20; G06K 9/4652; G06K 9/4661

See application file for complete search history.

(56) References Cited

U.S. PATENT DOCUMENTS

| | | | |
|---|---|---|---|
| 5,899,856 A | 5/1999 | Schoendorfer et al. | |
| 6,251,083 B1 | 6/2001 | Yum et al. | |
| 6,267,724 B1 * | 7/2001 | Taylor ................ | A61B 5/14532 128/898 |
| 6,706,099 B2 | 3/2004 | Sir et al. | |
| 6,773,671 B1 | 8/2004 | Lewis et al. | |
| 7,969,307 B2 | 6/2011 | Peeters | |
| 9,131,893 B2 * | 9/2015 | Faybishenko ..... | A61F 13/15699 |
| 9,532,762 B2 * | 1/2017 | Cho .................... | G06K 9/6217 |
| 10,195,294 B2 | 2/2019 | Tibbits | |
| 10,485,426 B2 * | 11/2019 | Liu ...................... | A61B 5/4854 |
| 2006/0206180 A1 | 9/2006 | Alcidi | |
| 2007/0160814 A1 | 7/2007 | Mercolino | |
| 2008/0107699 A1 | 5/2008 | Spigelman et al. | |
| 2009/0050491 A1 | 2/2009 | Brown | |
| 2009/0325221 A1 * | 12/2009 | Long ...................... | A61B 5/445 435/34 |
| 2010/0140108 A1 | 6/2010 | Roblin et al. | |
| 2011/0106000 A1 | 5/2011 | Jones et al. | |
| 2011/0295091 A1 | 12/2011 | Azer et al. | |
| 2012/0165626 A1 * | 6/2012 | Irina .................. | A61B 10/0064 600/316 |
| 2012/0187000 A1 | 7/2012 | Kahn et al. | |
| 2015/0126834 A1 | 5/2015 | Wang et al. | |
| 2015/0359469 A1 * | 12/2015 | Jacobs .................. | A61B 5/742 600/346 |
| 2016/0339120 A1 | 11/2016 | Tibbits | |
| 2017/0071536 A1 | 3/2017 | Tibbits | |
| 2017/0186160 A1 * | 6/2017 | Satish .................. | G06K 9/4604 |
| 2017/0325737 A1 | 11/2017 | Alvarez | |

FOREIGN PATENT DOCUMENTS

| | | | | |
|---|---|---|---|---|
| WO | WO-2012074509 A1 * | 6/2012 | ............. | A61B 5/318 |
| WO | WO-2015159280 A1 * | 10/2015 | .......... | G01N 33/497 |
| WO | WO-2016025468 A2 * | 2/2016 | .......... | A61B 5/6898 |
| WO | WO 2016/090189 | 6/2016 | | |
| WO | WO 2018/144627 | 8/2018 | | |

OTHER PUBLICATIONS

Supplementary information and figures for item U (Year: 2016).*
Bartolo et al., Microfluidic Stickers; Lab on a Chip 8:274-279) (Year:2007).
Bjerketorp et al., "Advances in preservation methods: Keeping biosensor microoganisms alive and active," Current Opinion in Biotechnology, 2006, 17:43-49.
Danino et al., "A synchronized quorum of genetic clocks," Nature, 2010, pp. 326-330, plus 9 pgs. of Supplementary Information, vol. 463.
Jia et al., "Electrochemical Tattoo Biosensors for Real-Time Noninvasive Lactate Monitoring in Human Perspiration" Analytical Chemistry 2013, 85: 6553-6560.
Lei et al., "Microbial Biosensors; Analytica Chimca Acta" 568 (2006) 200-210.
MacNab et al., "The Gradient-Sensing Mechanism in Bacterial Chemotaxis", Proc. Nat. Acad. Sci. USA, vol. 69, No. 9, pp. 2509-2512.
Martinez et al., "Three-dimensional microfluidic devices fabricated in layered paper and tape." PNAS 105(50): 19606-19611, 2008.
Prindle et al., "A Sensing array of radically coupled genetic 'biopixels'," Nature, 2012, pp. 39-44,vol. 481.
Su et al., "Microbial biosensors; A review", Biosensors and Bioelectronics, 2011, pp. 1788-1799, vol. 26.
PCT Application No. PCT/US2018/016281 International Search Report and Written Opinion dated May 29, 2018.
U.S. Appl. No. 15/162,438 Office Action dated Apr. 10, 2018.
U.S. Appl. No. 15/162,438 Final Office Action dated Jul. 11, 2017.
U.S. Appl. No. 15/162,438 Office Action dated Jan. 23, 2017.
U.S. Appl. No. 15/358,415 Final Office Action dated Mar. 29, 2019.
U.S. Appl. No. 15/358,415 Office Action dated Nov. 2, 2018.
U.S. Appl. No. 15/358,415 Final Office Action dated Apr. 9, 2018.
U.S. Appl. No. 15/358,415 Office Action dated Sep. 19, 2017.
U.S. Appl. No. 15/451,065 Office Action dated May 24, 2019.
U.S. Appl. No. 16/268,430, Skylar J.E. Tibbits, Programmable Bacterial Tattoo, filed Feb. 5, 2019.
U.S. Appl. No. 16/528,362, Skyler.
PCT Application No. PCT/US2018/016281 International Preliminary Report on Patentability dated Aug. 6, 2019.
U.S. Appl. No. 15/358,415 Final Office Action dated Sep. 28, 2020.
U.S. Appl. No. 15/451,065 Office Action dated Aug. 14, 2020.
U.S. Appl. No. 15/358,415 Final Office Action dated Aug. 23, 2018.
U.S. Appl. No. 15/358,415 Final Office Action dated Mar. 11, 2020.
U.S. Appl. No. 15/451,065 Final Office Action dated Feb. 11, 2020.
U.S. Appl. No. 15/358,415 Final Office Action dated May 6, 2021.
U.S. Appl. No. 15/451,065 Final Office Action dated Mar. 11, 2021.
U.S. Appl. No. 15/451,065 Office Action dated Jul. 2, 2021.

* cited by examiner

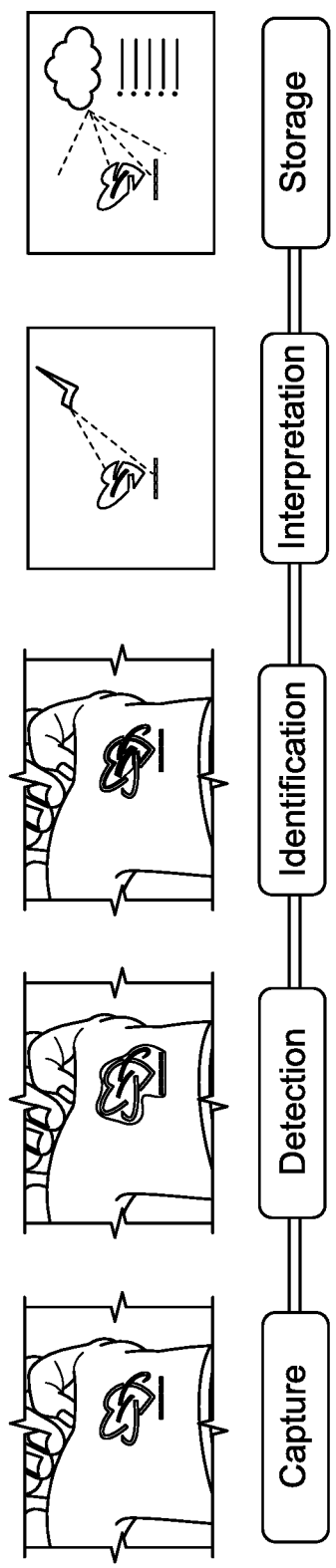
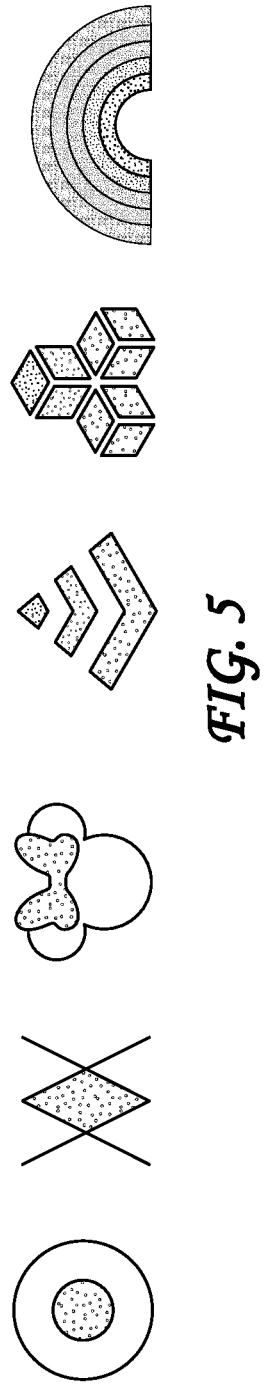

CUMULATIVE BIOSENSOR SYSTEM TO DETECT ALCOHOL

CROSS-REFERENCE TO RELATED APPLICATIONS

The present patent application is a continuation of International patent application number PCT/US18/16281 filed Jan. 31, 2018, which claims the priority benefit of U.S. provisional patent application No. 62/452,579 filed Jan. 31, 2017, the disclosures of which are incorporated by reference herein.

BACKGROUND OF THE INVENTION

1. Field of the Invention

The present invention generally relates to biosensors. More specifically, the present invention relates to cumulative biosensor systems for detecting alcohol.

2. Description of the Related Art

The usage of alcohol has many negative health and economic effects on individuals as well as society. In the United States (US) alone, excessive alcohol use led to approximately 90,000 deaths in the last year and is responsible for 10% of deaths in working-age adults, making alcohol-related deaths the fourth leading preventable cause of death. In addition, the economic burden of excessive alcohol consumption is enormous. In 2006, this cost was estimated at $223.5 billion in the US, or approximately $700 per individual.

The current market for alcohol monitoring technologies is primarily catered to alcohol enforcement at the government and business level. And while there are consumer grade options on the market, these available devices have major practical limitations for widespread use. They are bulky, electronics-dependent, and expensive. Even so called personal breathalyzers are only small enough to fit on a keychain. Moreover, these devices require active and "correct" use by the customer; i.e. customers must blow into the device in a specific way, for a set amount of time, or they may get an incorrect reading (6). This active use may also carry a strong stigma preventing true widespread use. The ability to conceal or personalize current breathalyzers and transdermal BAC devices does not exist today, as their electronics dictate a certain arrangement and size. Finally, since breathalyzers are not continuously sensing devices, they cannot offer a continuous cumulative readout of one's alcohol consumption.

Alcohol may further be linked to certain crimes, including date rapes which inflict a profound emotional and physiological impact on victims. Recent studies, conducted by the University of Iowa, which include victims of attacks at US college campuses, highlight both the emotional and staggering victimization costs (up to $151,423 in one instance).

There is, therefore, a need in the art for improved systems and methods for cumulative biosensor-based detection of alcohol.

SUMMARY OF THE CLAIMED INVENTION

The present invention includes a wearable biosensor that detects cumulative alcohol consumption, as well as an associated computing device application. In particular, the wearable biosensor is capable of detecting cumulative consumption of alcohol over time (e.g., since the biosensor was applied). As such, the biosensor readings differs from presently known methods of measuring alcohol consumption (e.g., Breathalyzer), which reflect only a current level of alcohol content. The biosensor described herein, however, reflects a cumulative amount of alcohol that has been consumed over the course of time since the biosensor was first applied (e.g., throughout the course of an evening). The detected accumulation of alcohol may be reflected in a variety of ways, including colors (and gradients of the same), as well as other visual and sensory means.

In one embodiment, an alcohol monitoring solution is offered that addresses many problems discussed above. Furthermore, such solution may appeal to a significantly larger market and user demographic, as learned from surveying 250 subjects across age, sex, education, drinking habits, and geography in the US. For example, a statistically significant indicator from these surveys was that women who drink casually are the most likely user segment to wear an electronics-free temporary tattoo that indicates alcohol levels via colorimetry. The form factor may serve as an adequate safety net, for example, during a date.

The ability to monitor alcohol consumption in a cumulative fashion by simple means has the potential to raise awareness of alcohol usage and could promote a healthier lifestyle across a wide user demographic, including young adults. For example, in cases where an individual's habitual drinking is gradually becoming more common, the device described herein could help identify and prevent a nascent negative trend developing into a severe health condition. In general, by addressing alcohol-related problems at their onset and throughout their development, the present invention may contribute more effectively to the mitigation of the health and economic burdens that such alcohol-related problems eventually devolve into.

Some embodiments may include a wearable instantaneous alcohol biosensor, as well as a related biosensor that detects cumulative alcohol levels. To allow for the option of tracking values electronically over longer periods of time, computer vision algorithms may be developed and trained to permanently record and interpret cumulative alcohol levels for the individual. Electronic tracking may allow for further guidance and awareness, and enabling anonymized data collection for research purposes.

BRIEF DESCRIPTION OF THE FIGURES

FIG. 4A illustrates exemplary capture of raw image using smartphone camera.

FIG. 4B illustrates exemplary detection of a temporary tattoo on skin.

FIG. 4C illustrates exemplary identification of the different elements of the temporary tattoo against a reference.

FIG. 4D illustrates exemplary analysis and interpretation of alcohol concentration values based on shape and color values at specific environmental conditions.

FIG. 4E illustrates exemplary storage of all data collected including the temporary tattoo extracted shape but excluding actual photographic images.

FIG. 5 illustrates a variety of customized designs for wearable alcohol biosensors.

DETAILED DESCRIPTION

The present invention includes a wearable biosensor that detects cumulative alcohol consumption, as well as an associated computing device application. In particular, the wearable biosensor is capable to detecting cumulative consumption of alcohol over time (e.g., since the biosensor was applied). As such, the biosensor readings differs from presently known methods of measuring alcohol consumption (e.g., Breathalyzer), which reflect only a current level of alcohol content. The biosensor described herein, however, reflects a cumulative amount of alcohol that has been consumed over the course of time since the biosensor was first applied (e.g., throughout the course of an evening). The detected accumulation of alcohol may be reflected in a variety of ways, including colors (and gradients of the same), as well as other visual and sensory means.

In addition, an associated computing device application may be optionally used with the wearable biosensor to track alcohol consumption trends over longer periods of time. Such an application may receive input regarding the reaction exhibited by the wearable biosensor indicating a cumulative amount of alcohol that has been detected. Such input may occur in the form of camera image, user input (e.g., selecting from a menu), or a wireless communication (e.g., in embodiments where the wearable biosensor may be coupled to a radio transmitter). Such input may be evaluated to determine what level of cumulative alcohol consumption is indicated and stored. The input may further be analyzed in context with previous input associated with the same user to identify trends, anomalies, and various other health or physical conditions of interest. In some embodiments, the application may further be trained and calibrated for more accurate or more detailed, granular results.

Figure 1:
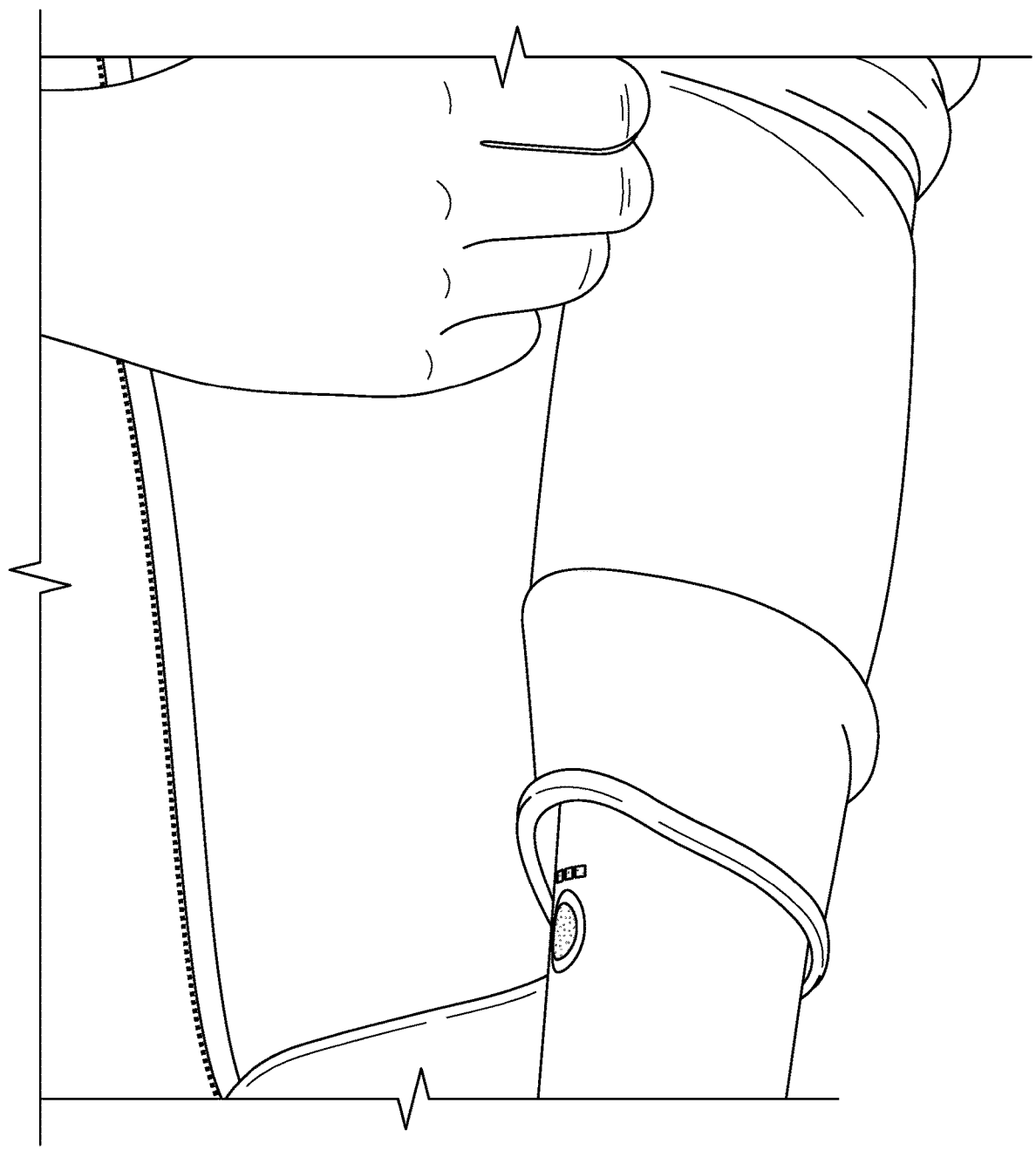
FIG. 1 illustrates an exemplary temporary tattoo that may be part of a wearable biosensor system for cumulative detection of alcohol.

Some embodiments may include a wearable, electronics-free, cumulative alcohol biosensor, and an optional mobile companion app. FIG. 1 illustrates an exemplary temporary tattoo that may be part of a wearable biosensor system for cumulative detection of alcohol. For example, an enzymatic reaction may be calibrated for variable sweat flow rates results in a colorimetric output correlated to the amount of ethanol circulating in the blood since the sensor was applied. Further embodiments may include a new computer vision pipeline that includes the use of recent artificial intelligence (AI) techniques to capture a raw image, detect the cumulative biosensor under diverse conditions, identify color changes, interpret the color changes with respect to the cumulative alcohol levels, and store this information for the user. Such functionalities make significant progress along a product development strategy that includes the following product differentiators:

Passive, continuous, and cumulative. Effortlessly raises awareness about a user's overall alcohol consumption patterns and how they may be changing over time.

Easy to wear, learn, and use. Worn much like a regular temporary tattoo or sticker, a wearable biosensor relies on the observation of color changes with the unaided eye, without strictly requiring the use of a separate device or application to understand the sensor; i.e., the tattoo is the user interface. A smartphone application may be offered to users as an option, not a requirement, thus maintaining a low threshold for user adoption while allowing smartphone users to track values over longer periods of time, and eventually providing other services and up sale opportunities.

Low cost. Whereas currently available solutions are electronics-dependent, the biosensors described herein are not.

Greater privacy and control of information encourages more people to wear an alcohol biosensor. Wearable alcohol biosensors can have a semi-arbitrary or user-specific design, potentially concealing information such that only the user understands its meaning. It can also be placed on different parts of the body, e.g. in the underarm or on the chest. When noticed, it bypasses the perception of being a medical device, thereby reducing the associated risk of stigmatization.

Figure 2D:
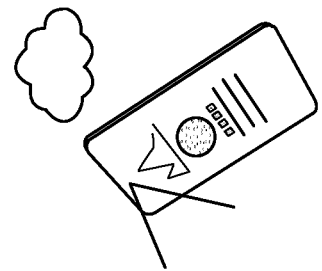
FIG. 2D illustrates an alternative exemplary implementation including an associated application for use with a temporary tattoo that may be part of a wearable biosensor system for cumulative detection of alcohol.
Figure 2C:
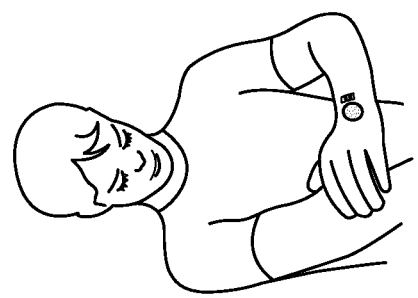
FIG. 2C illustrates an exemplary implementation of a temporary tattoo that may be part of a wearable biosensor system for cumulative detection of alcohol.
Figure 2B:
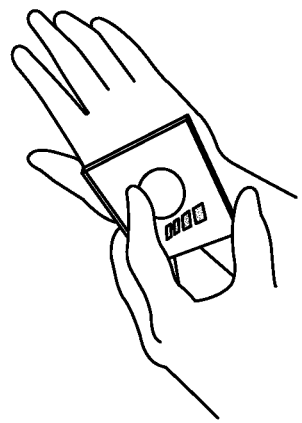
FIG. 2B illustrates an exemplary application of a temporary tattoo that may be part of a wearable biosensor system for cumulative detection of alcohol.
Figure 2A:
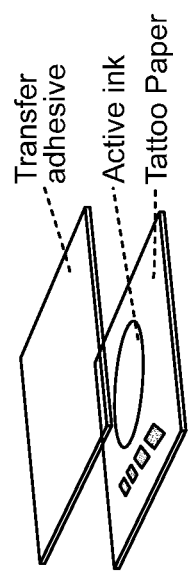
FIG. 2A illustrates an exemplary composition for a temporary tattoo that may be part of a wearable biosensor system for cumulative detection of alcohol.

FIGS. 2A-D illustrates various aspects to temporary tattoos that may be part of a wearable biosensor system for cumulative detection of alcohol. FIG. 2A illustrates an exemplary composition of a temporary tattoo that includes transfer adhesive, active ink, and tattoo paper. A formulated alcohol active ink may be screen printed onto tattoo paper alongside a spectrum of traditional inks that act as reference colors for the user.

FIG. 2B illustrates an exemplary application of a temporary tattoo that may be part of a wearable biosensor system for cumulative detection of alcohol. The combination of inks may be transferred or applied to the skin of the user in much the same way a temporary tattoo may be applied. For example, after removal of the transfer adhesive film, the temporary tattoo paper (printed with ink and associated with adhesive) is ready for application to skin. Tattoo paper with ink is firmly pressed to skin for 20-40 seconds after which water is applied to the back of the tattoo paper, facilitating release of the transfer paper. Transfer paper is removed from the skin leaving the desired active ink allowing for cumulative alcohol levels to be visualized and compared against reference colors.

FIG. 2C illustrates an exemplary implementation of a temporary tattoo that may be part of a wearable biosensor system for cumulative detection of alcohol. Once applied to the skin, sweat from the skin is absorbed into the active ink layer, where colorimetric changes allow for easy visualization.

FIG. 2D illustrates an alternative exemplary implementation including an associated application for use with a temporary tattoo that may be part of a wearable biosensor system for cumulative detection of alcohol. A mobile application downloaded onto a mobile device, for example, may allow for optional electronic tracking and simple quantification. Sensor levels can be monitored and recorded on an optional companion application that allow users to keep track of their alcohol usage for longer periods of time.

Design and characterization of a cumulative alcohol biosensor.

One embodiment may include an instantaneous electronics-free, transdermal blood alcohol content (BAC) biosensor in the form of a temporary tattoo. A wide variety of ethanol-sensing formulations may be provided based on the particular design of the biosensor. Such formulations may not only sense ethanol at a point in time, but also sense and represent its accumulation over time. The design of the temporary tattoo may therefore be configured so as to be present a visual indication system of such accumulation.

A toolkit of the temporary tattoo form factor and novel active ink formulations may be used to create a biosensor that is driven by the amount of alcohol consumed since the sensor was applied. At the core of the sensor is the active ink formulation. The formulation is based on the reaction of alcohol dehydrogenase (ADH), which alongside color changing tetrazolium salts form the active ink. Upon ethanol reaching the active ink containing ADH, the enzyme metabolizes ethanol to acetaldehyde and reduces NAD+ to NADH. NADH then transfers electrons through the electron acceptor phenazine methosulfate (PMS) to a tetrazolium salt, yielding a colored product.

Alongside the active ink, a series of graded reference colors may be printed. These colors may allow the users to immediately develop a qualitative sense of their cumulative alcohol consumption with the unaided eye.

Figure 3A:
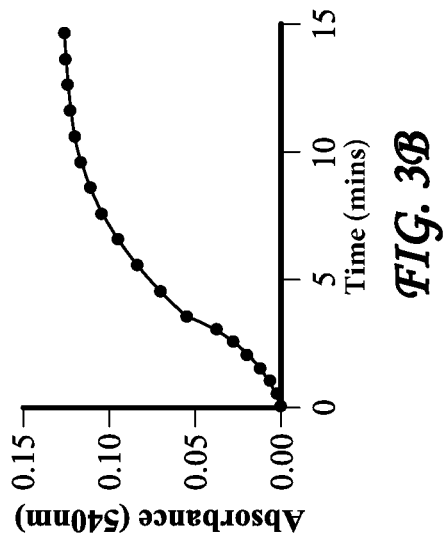
FIG. 3A is a graph correlating alcohol percentages to color-strength of an exemplary alcohol-sensing ink formulation.

FIG. 3A is a graph correlating alcohol percentages to color-strength of an exemplary alcohol-sensing ink formulation. Using one alcohol sensing formulation, concentrations of ethanol in solution and measured color using both visible and spectrophotometric detection may be scanned.

Figure 3B:
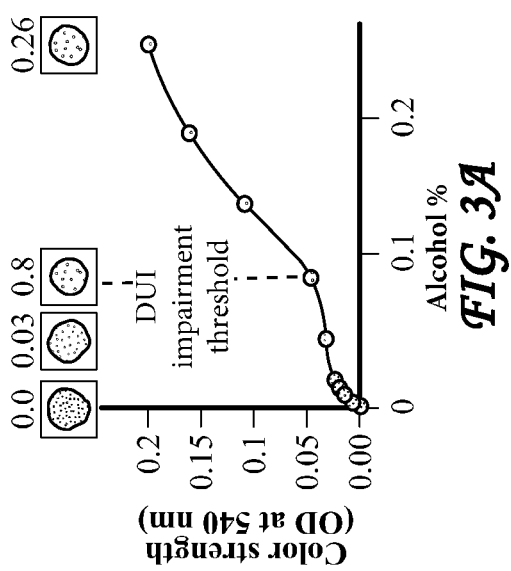
FIG. 3B is a graph illustrating color change kinetics of an exemplary alcohol-sensing ink formulation.

FIG. 3B is a graph illustrating color change kinetics of an exemplary alcohol-sensing ink formulation. The graph illustrates saturation within 10 minutes of ethanol addition at 0.15%.

Figure 3C:
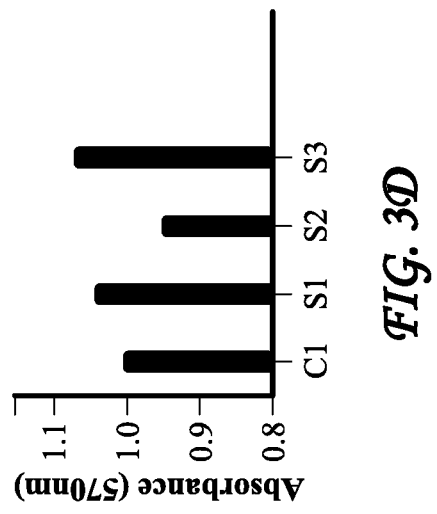
FIG. 3C is a graph correlating sweat concentrations with color absorbance change of an exemplary alcohol-sensing ink formulation.

FIG. 3C is a graph correlating sweat concentrations with color absorbance change of an exemplary alcohol-sensing ink formulation. Specifically, the graph illustrates absorbance (color) change measurements with varied sweat sodium (Na+) and chloride (Cl−) concentrations, where high activity was maintained across several alcohol concentrations.

Figure 3D:
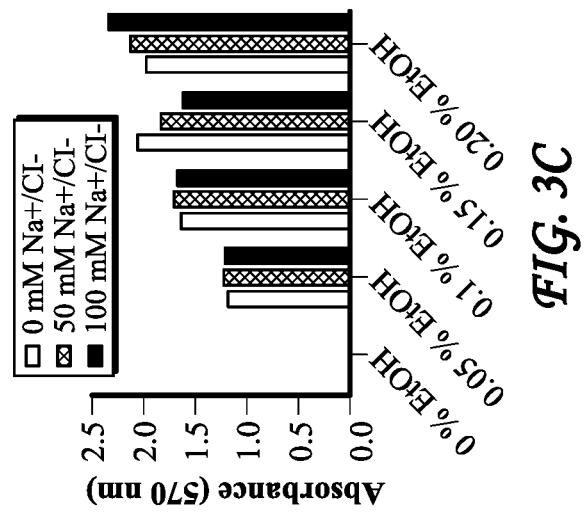
FIG. 3D illustrates exemplary sweat samples compared to a control solution.

FIG. 3D illustrates exemplary sweat samples compared to a control solution. Three human sweat samples collected spiked with 0.1% ethanol, showing activity is maintained relative to a control solution with 0 mM Na+.

An active ink formulation may include a tetrazolium salt such as 3-(4,5-Dimethylthiazol2-yl)-2,5-Diphenyltetrazolium Bromide (MTT), as well as commercially available ADH and PMS. The ink may be applied to the tattoo paper via silk screening. Because the product of MTT reduction, formazan, is insoluble, its formation is an irreversible reaction, resulting in increased color change as more ethanol is absorbed from the sweat (9). Thus, as the user consumes more ethanol, more ethanol is excreted in the sweat over a longer period of time and collected by the sensor, resulting in increased color intensity that can be used as a readout of cumulative consumption. Ethanol excretion in sweat is mainly independent of sweat flow rate (10), thus producing a robust cumulative metric across different conditions.

To characterize the formulations of a colorimetric reaction mixture, solution mixtures may be assayed in 24 and 48 well plates using spectrophotometry in a Tecan M200 plate reader. Standardized 0 to 0.3% ethanol solutions may be used to confirm colorimetric readout changes by absorbance at 540-570 nm with the use of the insoluble MTT. Reproducibility may be tested across different types of sweat by measuring the same 0 to 0.3% ethanol solutions in 10-100 µL solutions of 0-100 mM Na+ and Cl− to mimic the known ranges in sweat concentrations. Solutions of manually collected sweat spiked with 0 to 0.3% ethanol may subsequently be applied to the wells. Reversible ethanol sensing reactions may also be characterized as presented in FIG. 3A-3D. Here, the absorbance may be characterized at 540 nm as a measure of color change and measure the kinetics of the color changing reaction for several reactions (FIG. 3B). For the irreversible reaction described herein, the kinetics of ethanol sensing may be tuned such that the reaction does not saturate. Small volumes of ethanol-spiked sweat solutions may be added at typical sweat rates that may lead to further color change and simulate the cumulative ethanol readout. The amount of ethanol added to these reactions may be correlated to an estimated amount of ethanol molecules originating from the sweat, which may be calibrated to the amount of ethanol consumed (in grams).

Having formulated the chemical reaction mixture, different patterns may be screen printed onto paper substrates to test the kinetics of the colorimetric reaction mixture. Screen printing may require high viscosity and thixotropy of the printed fluid, previously developed and the use of food-grade thickeners with established safety profiles including xanthan gum, gum Arabic, corn starch, tapioca starch and carboxymethylcellulose (CMC). Rigorous characterization of the screen printing resolution properties may be done using microscopy and other approaches, determining that a 4% w/v carboxymethylcellulose (CMC) solution results in appropriate rheological properties with a uniform suspension of the reaction mixture. Using this mixture as a starting point for the cumulative alcohol biosensor, the kinetics and color changes of the ethanol sensing reaction may be assayed on transfer paper using time-lapse photography, and then analyze the color changes over time using ImageJ (13). The same procedure may be followed as with the previous mixtures, assaying solutions with varied ethanol and salt contents as well as sweat with predefined ethanol content.

Data analysis and statistics: The data generated in this section may resemble the data presented in FIGS. 3A-D. Absorbance measurements of the cumulative alcohol readout in the cases of water, defined salt concentrations, and collected sweat samples may be done in triplicate and reported with standard errors when plotted. For the sensor readouts on paper, measurements may be collected using a color camera, where 3-5 independent regions of interest may be analyzed for color change values and plotted with their variation. Measurements in this aim are expected to be normally distributed and statistical tests and analyses may be performed using Graphpad Prism software. These images and annotations may also be used to begin training the computer vision algorithms to be developed for the mobile application.

Expected outcomes and alternatives: Developing and characterizing the cumulative alcohol-level sensor may be completed within six months. Reformulation for the cumulative ethanol readout with the irreversible dye MTT may follow a similar path, but may require adjustment of the chemical formulations and kinetics for creating the appropriate dynamic range, including grading the reference colors. Determining such range is a key factor in determining the final active product life since it limits the number of drinks before the wearable needs to be renewed. A limit may be defined high enough for at least two days of heavy drinking. Also, if the kinetics of the MTT reaction are not desirable, other salts, like nitro blue tetrazolium (NBT) (15), may be used. Because it is inert, the use of CMC as a resuspension medium for screen-printing is not expected to affect the chemical reactions in the mixture, but if there are any undesired effects, other thickeners like those listed above may be used. If screen printing produces solutions that are too viscous and inhibit the reaction kinetics, dilution may occur before screen printing, or an alternative bioprinting inkjet method for deposition may be used. Lastly, if the reaction with ADH does not function as expected, other enzymes such as alcohol oxidase (AOX), which is known to be compatible with such salts, may be used.

If it is determined that the graded reference colors are not an ideal readout system, a different gradation approach may be used. In such an approach, the sensor may consist of multiple printed sections that reflect a gradient of values, like an 'energy bar" interface underneath the heart-shaped design illustrated as a series of squares in FIG. 4A. These sections may be individually calibrated such that they can only be activated once a specific cumulative ethanol content has been reached. This approach could eliminate a substantial amount of guesswork and interpretation on the user's part, however it may require much more specific ink formulations.

Another embodiment may include an optimized sweat collection layer that operates under diverse conditions, and that prevents the active ink from being in direct contact with the skin. Such a product may be tested in controlled and observational studies involving a representative sample of human subjects. Several sweat collecting—and inducing—methods exist that are compatible with the methods described herein. More active ink colors using different salts may be used, thus enabling further customization opportunities. Further embodiments may use a gradient tattoo UI when designing a biosensing temporary tattoo-like device. Thus, a user may customize their tattoo design to include (1) one more discrete and concealed (i.e. single tattoo design element changing in color) or (2) more explicit and potentially easier to understand (i.e. the gradient-based 'energy bars' approach).

Unaided-eye interpretation of color changes in sensor representing the cumulative levels of simulated transdermal alcohol concentrations over a 48-hour period with 90% accuracy.

Development of computer vision algorithms to track cumulative alcohol levels.

Wearable alcohol biosensors do not require electronic devices to read cumulative alcohol concentration values, thus contributing to targeting of a wider user demographic when compared to the current state of electronics-dependent devices. However, some users may prefer to use a smartphone app to track cumulative values over longer periods of time.

By giving the option to these users to capture and store values electronically, a future application may also provide other services such as trends analysis, and provide guidance or coaching Recognizing tattoos and interpreting them is an active area of research, faced with challenges that include their arbitrary design, and arbitrary placement—and deformation—when applied on different skin surfaces. An important part of the existing research focuses on features outside of the scope of alcohol biosensing (e.g. in criminology). A computer vision pipeline may be provided that is tailored to reading biomarker values and that tracks cumulative concentration values from a semi-arbitrarily designed temporary tattoo-like cumulative alcohol biosensor that can be placed on different parts of the body. Such a pipeline is composed of five modules: capture, detection, identification, interpretation, and storage.

The first module (FIG. 4A) may rely on a conventional smartphone's camera to take a raw image of the biosensor placed on the skin. The second module (FIG. 4B) uses the raw image as an input to detect the biosensor—a 2D surface—on a skin area of the body—a 3D model. Because an important differentiator of a wearable alcohol biosensor is that it can be easily customized to have a range of shapes placed on a skin surface, detection may use a convolutional neural network (CNN) for image patch labeling. In such an embodiment, a sliding window is used to classify each region traversed as either belonging or not to a tattoo. The module output is a masked image region and the specific deep learning architecture to achieve this assumes a model similar to AlexNet.

Training of the CNN may happen initially on temporary tattoos printed with regular inks. Training may always include a representative sample of skin types along the Fitzpatrick phototyping scale. A third module (FIG. 4C) performs feature extraction from the masked image by extending a version of Fast Retina Keypoint (FREAK). The modification is based on work originally described to detect logos from documents using a version of the scale invariant feature transform (SIFT). FREAK key descriptors generally perform faster on embedded systems such as smartphones. Some approaches may be based on detection of logos since in the beginning the biosensors may be composed of simple strokes and filled areas. Further refinements or other methods altogether may be used later for more sophisticated designs. Regarding future user customization of the design of a tattoo, the masked region of interest—the input to this module—may be matched against a reference shape in a dataset, since customized tattoos may be initially designed or uploaded through a mobile app. The output of this module is the extracted shape and its associated reference shape. The next module (FIG. 4D) interprets the differences between the extracted and reference shapes to assess the cumulative alcohol concentration values. As part of this process the extracted shape goes through a color normalization method to eliminate the effects of illumination, preserving the inherent colors of the sensor and reference colors, and only allowing color variations related to the cumulative alcohol concentrations. This method assumes the illumination to be reasonably well modelled as blackbody radiation. Also, the extracted shape is treated as a deformation of the reference shape. It is defined mathematically by mapping from the reference shape x to the deformed shape y by a transformation function.

At this point, the reference shape may be populated with normalized color values from the extracted shape across its surface area. To assess the cumulative alcohol concentration levels, calibration may be done by running a more granular sliding window of n×n pixel size to traverse the color-populated reference shape. In each new region, color value may be matched against the color versus concentration curves calibrated as discussed above. Additionally, the color curves may be color-normalized before use. Finally, the last module (FIG. 4E) stores all the data collected including the extracted shape but excluding actual photographic images in remote servers, thus helping preserve user privacy and the potential upload of non-sensor images.

Expected outcomes and alternatives: The various aspects described herein that can be applied to a range of sensors sharing the temporary tattoo-like form factor, including the cumulative alcohol monitoring biosensor described herein, or the previously developed instantaneous alcohol monitoring sensor. Modules may be added or improved while also training and calibrating the pipeline for the specific cumulative alcohol sensing application described herein. Highly qualitative data of cumulative alcohol values may be collected and used for training and calibrating until there is a more robust and semi-quantitative solution in place, which may be specific to a user. Reference colors may be used on the temporary tattoo, using the color versus concentration curves recorded as discussed above, thus allowing for an increase in accuracy. As described herein, calibrating the pipeline may allow for capture of a gradient tattoo UI (i.e. the 'energy bars' approach), where assessment of biosensor values may be easier. Also, because different smartphone models have different native RGB color spaces, color transformation techniques may be applied to a common color space using the full camera profile when available, or by using a standard color matrix.

Convolutional Neural Network (CNN) described for the detection module may be trained, thereby further increasing its robustness to detect a temporary tattoo at a wider range of camera angles, lighting conditions, skin types, and parts of the body. Other aspects of the pipeline may be enhanced including local storage, which may happen under a commercial setting integrating with services provided by third party companies or platforms such as Apple HealthKit. In general, the companion application may be robust enough to be ready to be used by consumers, initially during controlled and observational studies, and later in a commercial setting. Being user privacy protection a high concern for any consumer-oriented alcohol monitoring application, in addition to the use of standard user data encryption methods, commercially available services that involve Differential Privacy may be integrated in systems described herein, where the information stored in remote servers is randomly distorted in known statistical quantities, thus preventing anybody from pinpointing specific user data to an individual.

Computer vision interpretation of data color changes in sensor representing the cumulative levels of simulated transdermal alcohol concentrations over a 48-hour period with 90% accuracy.

FIG. 5 illustrates a variety of customized designs for wearable alcohol biosensors. Such designs may include a single active ink used on a single design element. Further designs may include multiple active inks used on multiple design elements, each becoming visible at different cumulative alcohol concentration levels, forming a gradient of cumulative values.

The detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claim.

What is claimed:

1. A method performed by a processor executing instructions stored in memory for detecting cumulative ethanol consumption, the method comprising:
receiving input indicative of a plurality of reactions at a plurality of corresponding sections of a wearable biosensor at a point in time, wherein the reactions occur in response to detection of ethanol consumption;
identifying the plurality of corresponding sections of the wearable biosensor from the received input including comparing the corresponding sections of the wearable biosensor to that of one or more reference shapes stored in a database memory by using a transformation function;
identifying the cumulative amount of ethanol consumption by evaluating each of the plurality of corresponding sections of the wearable biosensor relative to a corresponding reference parameter, wherein each of the corresponding sections of the wearable biosensor is activated at a different ethanol consumption level along a gradient;
storing the cumulative amount of ethanol consumption in memory, wherein the cumulative amount of ethanol consumption is stored in association with the point in time; and
identifying a trend of the cumulative ethanol consumption over time.

2. The method of claim 1, wherein receiving the input comprises receiving an image of the wearable biosensor captured by a camera after the wearable biosensor visibly indicates the reaction.

3. The method of claim 2, wherein identifying the plurality of corresponding sections of the wearable biosensor from the received input further includes using a sliding window of a convolutional neural network for image patch labeling.

4. The method of claim 2, wherein identifying the plurality of corresponding sections of the wearable biosensor from the received input further includes extracting one or more masked image regions that define the corresponding sections of the wearable biosensor.

5. The method of claim 4, wherein extracting the masked image regions includes detecting keypoints that define a shape of the extracted masked image regions.

6. The method of claim 5, further comprising defining the shape of the extracted masked image region as a deformation of shape of the one or more reference shapes.

7. The method of claim 6, wherein comparing the corresponding sections of the wearable biosensor to the one or more reference shapes comprises mapping from the shape of the one or more reference shapes to the shape of the extracted masked image region by the transformation function.

8. The method of claim 2, further comprising normalizing the image for color to eliminate effects of illumination.

9. The method of claim 2, wherein evaluating each of the plurality of corresponding sections of the wearable biosensor relative to a corresponding reference parameter comprises:
detecting a color value of at least one corresponding section; and
matching the detected color value to a stored chart of calibrated color concentration values.

10. The method of claim 9, wherein matching the detected color value to the stored chart includes comparing the detected color value to a representative sample of skin types along a Fitzpatrick phototyping scale.

11. The method of claim 2, further comprising normalizing the image for color to preserve inherent colors of the image of the wearable biosensor and colors of one or more reference colors stored in a database memory.

12. The method of claim 2, further comprising normalizing the image for color to preserve color variations associated with the cumulative amount of ethanol consumption.

* * * * *